United States Patent
Popescu et al.

(10) Patent No.: US 7,492,871 B2
(45) Date of Patent: Feb. 17, 2009

(54) FOCUS/DETECTOR SYSTEM OF AN X-RAY APPARATUS FOR GENERATING PHASE CONTRAST RECORDINGS

(75) Inventors: Stefan Popescu, Erlangen (DE); Björn Heismann, Erlangen (DE); Eckhard Hempel, Fürth (DE); Christian David, Lauchringen (DE); Franz Pfeiffer, Brugg (CH)

(73) Assignee: Siemens Aktiengesellschaft, Munich (DE)

(*) Notice: Subject to any disclaimer, the term of this patent is extended or adjusted under 35 U.S.C. 154(b) by 0 days.

(21) Appl. No.: 11/700,140

(22) Filed: Jan. 31, 2007

(65) Prior Publication Data
US 2007/0183580 A1 Aug. 9, 2007

(30) Foreign Application Priority Data
Feb. 1, 2006 (DE) .................. 10 2006 004 976
Apr. 12, 2006 (DE) .................. 10 2006 017 291

(51) Int. Cl.
*G21K 1/00* (2006.01)
*G21K 1/12* (2006.01)

(52) U.S. Cl. ........................... 378/145; 378/19
(58) Field of Classification Search ............ 378/2, 378/62, 84–87, 70, 71, 145, 4, 19
See application file for complete search history.

(56) References Cited

U.S. PATENT DOCUMENTS

| | | | |
|---|---|---|---|
| 4,031,395 A | 6/1977 | LeMay | |
| 5,684,851 A * | 11/1997 | Kurbatov et al. | ............. 378/87 |
| 5,812,629 A | 9/1998 | Clauser | |
| 6,262,818 B1 | 7/2001 | Cuche et al. | |
| 6,713,767 B2 | 3/2004 | Wieczorek et al. | |
| 7,180,979 B2 * | 2/2007 | Momose | ............. 378/62 |

(Continued)

FOREIGN PATENT DOCUMENTS

DE 26 11 706 A1 2/1977

(Continued)

OTHER PUBLICATIONS

Weitkamp et al., "X-ray phase imaging with a grating interferometer", Optics Express 2005, vol. 12, No. 16, pp. 6296-6304.

(Continued)

*Primary Examiner*—Irakli Kiknadze
(74) *Attorney, Agent, or Firm*—Harness, Dickey & Pierce, P.L.C.

(57) ABSTRACT

A focus/detector system of an X-ray apparatus and a method for generating projective or tomographic phase contrast recordings, are disclosed. In an embodiment of the system, the system includes a beam source equipped with a focus and a focus-side source grating, arranged in the beam path and generates a field of ray-wise coherent X-rays, a grating/detector arrangement having a phase grating and grating lines arranged parallel to the source grating for generating an interference pattern, and a detector having a multiplicity of detector elements arranged flat for measuring the position-dependent radiation intensity behind the phase grating. Finally, the detector elements are formed by a multiplicity of elongate scintillation strips, which are aligned parallel to the grating lines of the phase grating and have a small period, whose integer multiple corresponds to the average large period of the interference pattern which is formed by the phase grating.

37 Claims, 8 Drawing Sheets

U.S. PATENT DOCUMENTS

| | | | |
|---|---|---|---|
| 2002/0070365 A1 | 6/2002 | Karellas | |
| 2005/0226376 A1 | 10/2005 | Yun et al. | |
| 2007/0183581 A1* | 8/2007 | Heismann et al. | 378/145 |
| 2007/0183582 A1* | 8/2007 | Baumann et al. | 378/145 |
| 2007/0183583 A1* | 8/2007 | Baumann et al. | 378/145 |

FOREIGN PATENT DOCUMENTS

| | | |
|---|---|---|
| DE | 197 50 337 A1 | 6/1998 |
| DE | 101 21 018 A1 | 10/2002 |
| DE | 10 2006 015 355.3 | 8/2007 |
| DE | 10 2006 015 356.1 | 8/2007 |
| DE | 10 2006 015 358.8 | 8/2007 |
| DE | 10 2006 017 290.6 | 8/2007 |
| DE | 10 2006 017 291.4 | 8/2007 |
| EP | 1 447 046 A1 | 8/2004 |
| EP | 1 119 798 B1 | 3/2005 |

OTHER PUBLICATIONS

D. Vaughan (ed.), "X-Ray Data Booklet", Lawrence Berkeley Laboratory, Berkley, 1986, pp. 2-28, 2-29.

U. Bonse and M. Hart, "An X-ray Interferometer", Appl. Phys. Lett., 1965, vol. 6, No. 8, pp. 155-156.

Ingal and Bellaevskaya, "X-ray plane-wave topography observation of the phase contrast from a non-crystalline object", J. Phys. D: Appl. Phys. 28, 1995, pp. 2314-2317.

R. Fitzgerald, "Phase-Sensitive X-Ray Interferometer", Physics Today, 53, 2000, pp. 23-26.

Chapman et al., "Diffraction enhanced x-ray imaging", Phys. Med. Biol. 42, 1997, pp. 2015-2025.

Wilkins et a., "Phase-contrast imaging using polychromatic hard X-rays", Nature 384, 1996, pp. 335-338.

V. Lehmann, The Physics of Macropore Formation in low Doped n-Type Silicon, J. Electrochemical Soc. 140 (10), 1993, pp. 2836-2843.

Bergmann, Schäfer, "Lehrbuch der Experimentalphysik", vol. 1, Mechanik, Akustik, Wärme, De Gruyter, Berlin, 1970, pp. 542-554.

Shack et al., J. Opt. Soc. Am. 61, 1971, p. 656.

Platt et al., "History and Principles of Shack-Hartmann Wavefront Sensing", Journal of Refractive Surgery, vol. 17, 2001, pp. 573-577.

F. Roddier, "Variations on a Hartmann theme", Opt. Eng. 29, 1990, pp. 1239-1242.

Primot et al., "Deconvolution from wave-front sensing: a new technique for compensating turbulence-degraded images", J. Opt. Soc. Am. 7(9), 1990, pp. 1598-1608.

J. C. Wyant, "White Light Extended Source Shearing Interferometer", Appl. Opt. 13, 1974, pp. 200-202.

C. L. Koliopoulos, "Radial grating lateral shear heterodyne interferometer", Appl. Opt. 19, 1980, pp. 1523-1528.

J. Primot, L. Songo, "Achromatic three-wave (or more) lateral shearing interferometer", J. Opt. Soc. Am. A, 12(12), 1995, pp. 2679-2685.

J. Primot, "Theoretical description of Shack-Hartmann wave-front sensor", Optics Communications, 222, 2003, pp. 81-92.

V. Ronchi, "Forty Years of History of a Grating Interferometer", Appl. Opt., 3(4), 1964, pp. 437-451.

Schroer et al., "Hard x-ray nanoprobe based on refractive x-ray lenses", Appl. Phys. Lett. 87, 124103, 2005.

M. Bavdaz, N. Gurker, "Coded Imaging X-ray Microprobe", X-Ray Spectrometry, 22, 1993, pp. 65-70.

Momose et al. "Tomographic image reconstruction using X-ray phase information", SPIE, vol. 2708, pp. 674-684.

Barty et al., "Time-gated medical imaging with ultrafast laser plasma x-rays", SPIE, vol. 2523, pp. 286-298.

C. J. Kotre, I. P. Birch, "Phase contrast enhancement of x-ray mammography: a design study", Phys. Med. Biol., 44, 1999, pp. 2853-2866.

Arfelli et al, "Low-dose phase contrast x-ray medical imaging", Phys. Med. Biol. 43, 1998, pp. 2845-2852.

Herrlin et al., "Contrast-Enhanced Radiography by Differential Absorption Using a Laser-Produced X-Ray Source", Investigative Radiology 32, 1997, pp. 306-310.

Grätz et al., "Time-Gated Imaging in Radiology: Theoretical and Experimental Studies", IEEE J. of selected Topics in Quantum Electronics, 2(4), 1996, pp. 1041-1048.

Murnane et al., "Ultrafast X-ray Pulses from Laser-Produced Plasmas", Science, vol. 251, 1991, pp. 531-536.

Krol et al., "Laser-based microfocused x-ray source for mammography: Feasibiliy study", Med. Phys. 24(5), 1997, pp. 725-732.

Piestrup et al., "A design of mammography units using a quasiminichromatic x-ray source", Review of Scientific Instruments, 72(4), 2001, pp. 2159-2170.

C. G. Schroer, B. Lengler, "Focusing Hard X Rays to Nanometer Dimensions by Adiabatically Focusing Lenses", Phys. Rev. Lett. 94, 054802, 2005.

Weitkamp et al.: X-ray phase imaging with a grating interferometer Optics Express, 2005, vol. 13, No. 16 p. 6296-6304.

Pfeiffer et al.: Phase retrieval and differential phase-contrast imaging with low-brilliance X-ray sources Nature Physics, 2006, vol. 2 p. 258-261.

Senoussaoui et al.: Thin-film solar cells with periodic grating coupler Thin Solid Films, 2004, vol. 451-452 p. 397-401.

* cited by examiner

FIG 6
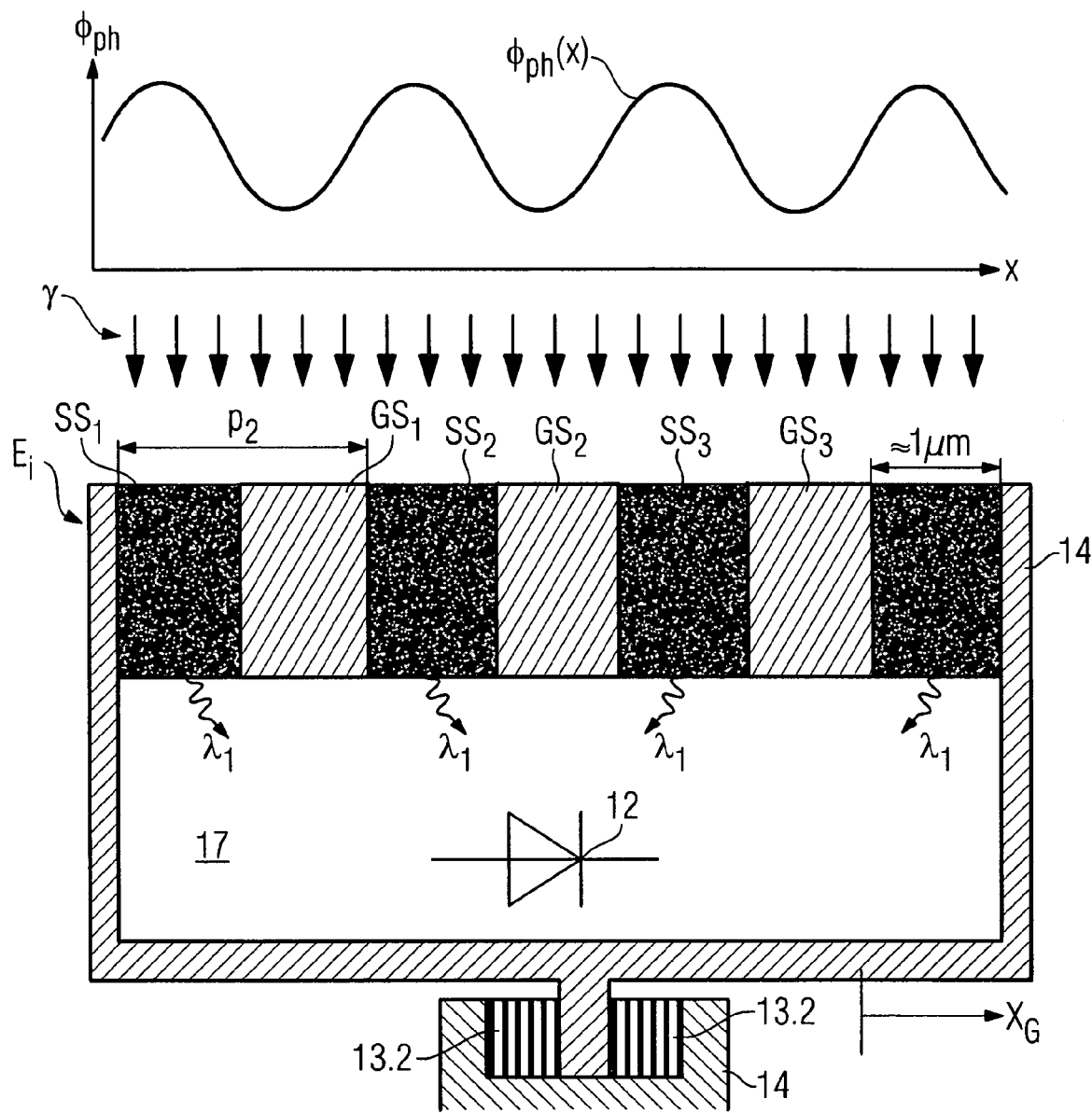
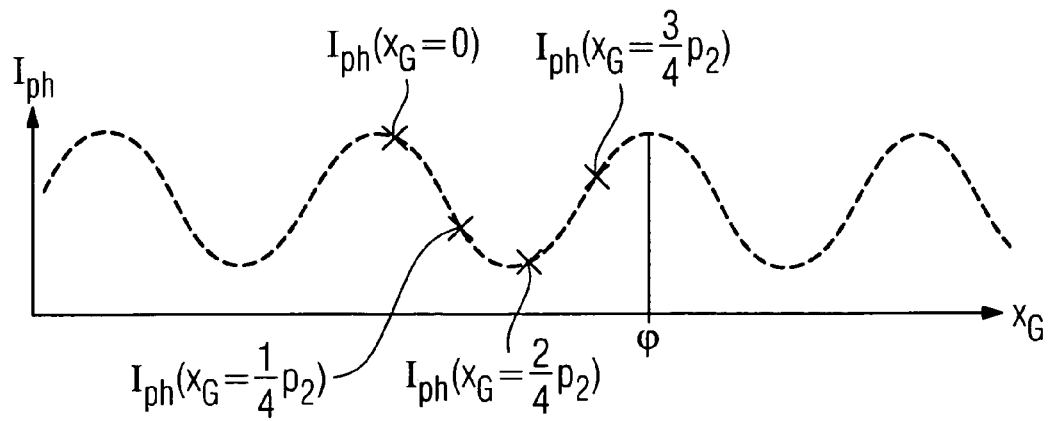

FIG 8
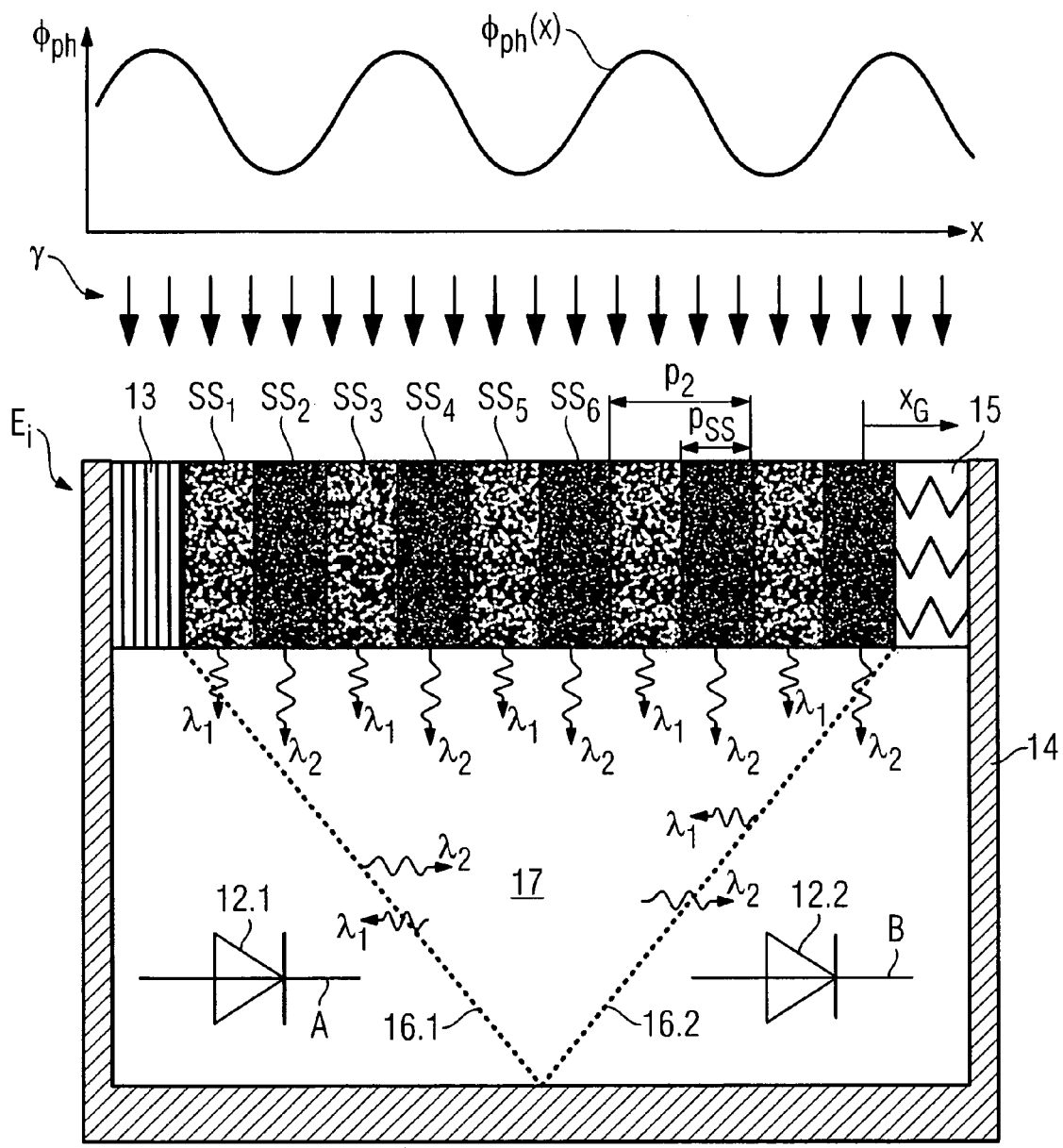
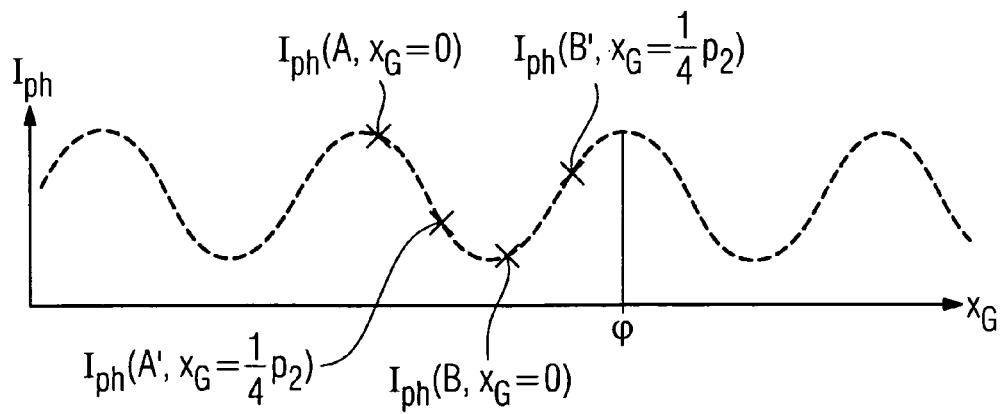

FOCUS/DETECTOR SYSTEM OF AN X-RAY APPARATUS FOR GENERATING PHASE CONTRAST RECORDINGS

PRIORITY STATEMENT

The present application hereby claims priority under 35 U.S.C. §119 on German patent application numbers DE 10 2006 004 976.4 filed Feb. 1, 2006, and DE 10 2006 017 291.4 filed Apr. 12, 2006, the entire contents of each of which is hereby incorporated herein by reference.

FIELD

Embodiments of the invention generally relate to a focus/detector system of an X-ray apparatus for generating projective and tomographic phase contrast recordings. For example, they may relate to one including a beam source having a focus, a detector arrangement for detecting the X-radiation and a set of X-ray optical gratings, for determining the phase shift when the X-radiation passes through a subject.

BACKGROUND

In computer tomography, tomographic recordings of a subject, in particular a patient, are generally made with the aid of absorption measurements of X-rays which pass through the subject, a radiation source generally being moved circularly or spirally around the subject and a detector on the opposite side from the radiation source, usually a multiline detector with a multiplicity of detector elements, measuring the absorption of the radiation when it passes through the subject. For tomographic image compilation, tomographic section images or volume data are reconstructed from the measured absorption data of all measured geometrical rays. Absorption differences in objects can be represented very well by these computer tomographic recordings, but regions with similar chemical composition, which naturally also have a similar absorptivity, can be represented only with insufficient detail.

It is furthermore known that the effect of the phase shift when a ray passes through a subject is substantially stronger than the absorption effect of the matter through which the radiation has passed. Such phase shifts are measured in a known way by using two interferometric gratings. With respect to these interferometric measurement methods, reference is made for example to "X-ray phase imaging with a grating interferometer, T. Weitkamp et al., Aug. 8, 2005/Vol. 12, No. 16/OPTICS EXPRESS".

In this method, coherent X-radiation passes through a subject, the X-radiation having passed through is guided through a grating pair and the radiation intensity is measured immediately after the second grating. The first grating generates an interference pattern, which forms an image of a Moiré pattern with the aid of the second grating on the detector lying behind. If the second grating is displaced slightly, then this likewise causes a displacement of the Moiré pattern, i.e. a change of the local intensity in the detector lying behind, which can be determined relative to the displacement of the second grating.

If the intensity change is plotted for each detector element of this grating, i.e. for each ray, as a function of the displacement distance of the second grating, then the phase shift of the respective ray can be determined. A problem, making it unsuitable for carrying out computer tomography of sizeable objects, is that this method requires a very small radiation source since coherent radiation is needed for forming the interference pattern.

The method presented in the document cited above requires either a radiation source with an extremely small focus, so that there is a sufficient degree of spatial coherence in the radiation used. When using such a small focus, however, then a sufficient dose power for examining a sizeable object is in turn not available. It is nevertheless also possible to use monochromatically coherent radiation, for example synchrotron radiation as the radiation source, but this makes the CT system very expensive to construct so that widespread application is not possible.

SUMMARY

This problem can be circumvented by arranging a first absorption grating inside the focus/detector combination in the beam path, immediately after the focus. The alignment of the grating lines is in this case parallel to the grating lines of the interference grating which follows after the subject.

The slits of the first grating generate a field of individually coherent rays with a particular energy, which is sufficient for generating the interference pattern known per se with the aid of the phase grating arranged behind the object in the beam direction.

In this way, it is possible to use radiation sources which have extents that correspond to normal X-ray tubes in CT systems or transmitted-light X-ray systems so that, for example, even well-differentiated soft tissue tomographs can now be made in the field of general medical diagnosis with the aid of X-ray devices.

A problem with this type of focus/detector combination is that on the one hand the analysis grating constitutes an additional sensitive component, which is cost-intensive to install and adjust.

In a development according to a further aspect of at least one embodiment of the invention, a better dose utilization is intended to be achieved than is possible when using an absorption spectrum, in which half the applied dose is always lost. Furthermore, at least three measurements need to be carried out respectively with a slightly displaced analysis grating for each ray in space, so that it is possible to determine the phase shift of the X-radiation on the respective ray path through the subject. This entails an increased time and adjustment outlay for the measurements, which is intended to be reduced.

In at least one embodiment of the invention, a focus/detector system is provided which allows simpler construction. The effect intended to be achieved according to a further aspect is to reduce the number of measurements required for determining the phase shift, or even to carry out just one measurement process on each ray in order to be able to generate projective or tomographic phase contrast recordings of a subject. According to a further aspect, better dose utilization is also intended to be achieved.

The Inventors, in at least one embodiment of the invention, have discovered that instead of the previously used analysis grating, it is possible to use detector elements which comprise a multiplicity of scintillation strips that subdivide the individual detector element in the direction of the grating lines of an upstream phase grating, so that the previously required analysis grating can be obviated. The individual scintillation strips may furthermore be configured so that they alternately emit different frequency light, which is selectively measured. This entails a simply configured grouping of different scintillation strips inside a detector element, summation being carried out over the individual groups without great circuit technology outlay. The frequency-selective measurement and emission of all the scintillation light in a common space thus achieves selective summation of all light events at the different scintillator materials arranged in a strip shape.

Depending on the number of groups which are formed and depending on the period with which the scintillation strips are arranged, i.e. depending on the fineness of the individual scintillation strips, it is therefore now possible to resolve an individual X-ray so that either the number of measurements with which a particular X-ray is sampled can be greatly reduced or, with a correspondingly high division of the scintillation strips, the average phase of the respectively considered X-ray can be determined directly with a single measurement of the scintillation strips dimensioned groupwise.

In at least one embodiment, improved or even optimal dose utilization is also achieved by such a strip-shaped structure of the detector elements without "dead regions", in which no measurement takes place. The full amount of the used dose to which the subject, in particular a patient, is exposed, is thus now used for the measurement and, unlike when an analysis grating is used, a part of the dose to which the patient has been exposed is not superfluously absorbed in the analysis grating.

According to the basic concept of at least one embodiment of this invention, the Inventors propose a focus/detector system of an X-ray apparatus for generating projective or tomographic phase contrast recordings, comprising:

a beam source having a focus and a focus-side source grating, which is arranged in the beam path and generates a field of ray-wise coherent X-rays, a grating/detector arrangement having a phase grating and grating lines arranged parallel to the source grating for generating an interference pattern, and a detector having a multiplicity of detector elements arranged flat for measuring the position-dependent radiation intensity behind the phase grating, wherein the detector elements are formed by a multiplicity of elongate scintillation strips, which are aligned parallel to the grating lines of the phase grating and have a small period, whose integer multiple corresponds to the average large period of the interference pattern which is formed by the phase grating.

With respect to the grating/detector arrangement, it is proposed that this should be designed and arranged so that it satisfies the following geometrical conditions:

$$p_2 = k \times p_s$$

$$p_0 = p_2 \times \frac{l}{d},$$

$$p_1 = 2 \times \frac{p_0 \times p_2}{p_0 + p_2}$$

$$d = \frac{l \times d^=}{l - d^=} \text{ with } d^= = \frac{1}{2} \times \left(\frac{p_1^2}{4\lambda}\right),$$

$$h_1 = \frac{\lambda}{2(n-1)}.$$

Here:

$p_0$=grating period of the source grating $G_0$,
$p_1$=grating period of the phase grating $G_1$,
$p_2$=large period of the scintillation strips $SS_i$, average spacing of the interference lines after the phase grating,
$p_s$=small period of the scintillation strips $SS_i$, distance from midline to midline of neighboring scintillation strips,
d=distance from the phase grating $G_1$ to the detector in fan beam geometry,
$d^=$=distance from the phase grating $G_1$ to the detector with parallel geometry,
k =1, 2, 3, 4, 5, . . . ,
l=distance from the source grating $G_0$ to the phase grating $G_1$,
λ=selected wavelength of the radiation,
$h_1$=bar height of the phase grating $G_1$ in the beam direction,
n=refractive index of the grating material of the phase grating.

In a first simple alternative embodiment, the Inventors propose that the focus/detector system be configured so that precisely one scintillation strip, which alternates with a detector grating structure made of non-scintillating material, is arranged inside each large period. In terms of metrology, while having a simple structure, this essentially achieves the same effect as when using an analysis grating with the need for multiple measurements of the same ray in order to determine the existing phase shift. In order to achieve good stability and a large absorption difference between grating gaps and grating lines, it may be favorable for the detector grating structure to be made of metal.

In another variant of the focus/detector system according to at least one embodiment of the invention, the Inventors propose to arrange precisely two scintillation strips made of different scintillation material, which generate light of different frequency f or different wavelength $\lambda_i$ according to the relationship $\lambda_i=c/f_i$, inside each large period, their sequence remaining the same over the entire detector element. This now makes it possible to utilize the detector surface optimally, since there are no longer any regions with radiation masking. In principle, this variant of the embodiment corresponds to a combination of two detector elements offset by half the large period, a detector material with different light emission properties respectively being used instead of the grating. Owing to the different frequencies of the light emissions, they can easily be measured separately from one another.

Although in this variant of a focus/detector system the number of measurement processes required is reduced from at least three to at least two since two measurement values per measurement are obtained for two sample points to determine the phase profile, an offset between the measurements is nevertheless required. To this end, for example, the Inventors propose, in at least one embodiment, that a device/method be provided for offsetting the scintillation strips perpendicularly to the longitudinal direction of the scintillation strips in the detector, which can generate a defined offset of the order of the small period of the scintillation strips. As an alternative, a device/method may be provided for offsetting the detector elements or for offsetting the entire detector perpendicularly to the longitudinal direction of the scintillation strips in the detector. What is important for this offset and the devices selected therefor, is that it should be carried out in a defined way in the size range of the small period. Piezo elements, for example, are particularly suitable for this.

In a further development of at least one embodiment of the inventive concept, in which a spatial offset is no longer categorically necessary, at least three scintillation strips made of different scintillation material, which generate light of different frequency, may be arranged inside each large period, here again their sequence remaining constant over the detector element. If this embodiment is used, then it is now possible for the spatial offset during the detection of the radiation intensity to be replaced by at least three frequency-selective measurements.

Although a spatial offset of the scintillation strips is not categorically necessary here, for error reduction it may nevertheless be more favorable to increase the number of sample points and to this end provide a device/method for offsetting the scintillation strips perpendicularly to the longitudinal direction of the scintillation strips in the detector, which can generate a defined offset of the order of the small period of the scintillation strips. As an alternative, the detector elements or the detector may also be offset. As mentioned above, piezo elements in particular are suitable for this.

The Inventors furthermore propose, in at least one embodiment, that a device/method be provided in the detector element which detect the light emissions of the scintillation strips of a detector element with different frequency separately according to frequency but summed over the entire detector element. Through such a configuration, it is possible to replace elaborate circuits for controlled groupwise combination of the scintillation strips of a detector element. The detector elements may furthermore be configured so that the scintillation strips emit their light with different frequencies at least partially into a mirrored space which adjoins frequency-selective light sinks, and each light sink includes a device/method for detecting the selected light.

In a first alternative embodiment, the light sinks respectively consist of a filter with a downstream photodiode, the filters respectively being selective for precisely one of the emitted frequencies of the scintillation strips.

Another alternative embodiment may reside in the light sinks being arranged in cascade fashion and respectively including a filter on the scintillator side with a photodiode, which limits the frequencies on one side so that a reduced number of frequencies is measured in the subsequent filter/photodiode set. With this variant the photodiodes are thus arranged in cascade behind filters, the filters increasingly cutting off the frequencies beginning on one side of the frequency spectrum. In this way, a photodiode on the side facing toward the input side of the light can detect the entire frequency spectrum and a respectively further restricted spectrum can be measured at each further photodiode, so that the intensity of individual spectral ranges can be determined.

According to the basic concept of at least one embodiment of the invention, the Inventors also propose an X-ray system for generating projective phase contrast recordings, which is equipped with at least one of the focus/detector systems described above. Such focus/detector systems may also be used in conjunction with an X-ray C-arc system for generating projective and tomographic phase contrast recordings or an X-ray CT system for generating tomographic phase contrast recordings.

Such X-ray systems may furthermore include a computation unit for controlling the detector and calculating the phase shift from a plurality of intensity measurements of the same ray.

A computation and control unit is also proposed, which contains program code that carries out the method described below during operation. A storage medium of an X-ray system or for an X-ray system is likewise proposed, which contains program code that carries out this method during operation of an X-ray system.

According to the basic concept of at least one embodiment of the invention, the Inventors furthermore propose a method for generating projective X-ray recordings of a subject, preferably of a patient, the method comprising:

the subject is irradiated by a beam of rays, each ray in space being defined with respect to direction and extent by the focus-detector element connecting line and the extent of the detector element, the average phase shift of each ray is measured in that, for this ray, the intensity of the radiation is measured with the aid of the fine structured scintillation strips at scintillation strips arranged groupwise and offset with respect to one another or positioned offset from one another, phase contrast recordings, the pixel values of which represent the average phase shift per ray, are compiled from the measured average phase shifts.

According to an example variant of an embodiment of the method, it is proposed that the various scintillation strips of a detector element emit light groupwise with different light frequencies during exposure and that this light be measured selectively with respect to the frequency but summed over the entire detector element.

A spatial offset of the scintillation strips perpendicularly to the grating line direction may furthermore be induced between two measurements of the same ray. In this case, the spatial offset of the scintillation strips should be induced by an amount less than the small period of the scintillation strips.

According to another variant of an embodiment, there are at least three different types of scintillation strips in a detector element, these are arranged uniformly alternating and one measurement for all emitted light frequencies is carried out per detector element and position, and the average phase shift of the measured X-ray is determined directly therefrom.

BRIEF DESCRIPTION OF THE DRAWINGS

The invention will be explained in more detail below with reference to example embodiments with the aid of the figures, only the features necessary for understanding the invention being represented. Here, the following references are used: 1: CT system; 2: first X-ray tube; 3: first detector; 4: second X-ray tube; 5: second detector; 6: gantry housing; 7: patient; 8: patient support; 9: system axis; 10: control and computation unit; 11: memory; 12, 12.x: photodiode; 13, 13.x: piezo element; 14: detector housing; 15: spring element; 16.x: filter; 17: mirrored space; A, B, C, D: measurement paths for scintillation strips of light emitted with different frequency; d: distance from the phase grating $G_1$ to the analysis grating $G_2$ or to the detector strips $SS_i$ in fan beam geometry; $d^=$: distance from the phase grating $G_1$ to the analysis grating $G_2$ or to the detector strips $SS_i$ with parallel geometry; $D_1$: detector; $E_i$: $i^{th}$ detector element; $F_1$: focus; $G_0$: source grating; $G_1$: phase grating; $G_2$: analysis grating; $GS_x$: grating strips; $h_0, h_1, h_2$: height of the grating bars; $I(E_i(x_G))$: measured intensity at the detector element $E_i$ with the grating offset $x_G$; $I_{ph}$: measured intensity of the photon flux; l: source grating-phase grating distance; P: patient; $p_o, p_1, p_2$: period of the grating lines; $p_{ss}$: period of the scintillation strips; $Prg_n$: program; S: system axis; $S_1, S_2$: X-rays; $SS_x$: scintillation strips; w: extent of the focus; $x_G$: offset of the analysis grating; $\lambda$: wavelength of the X-radiation in question; $\lambda_i$: wavelength of the light in question; $\phi$: phase shift; $\gamma$: X-radiation; $\Phi_{ph}(x)$: photon flux at the position x of a detector element; $\Phi_{ph}$: photon flux; v: extent of a voxel.

The figures show the following in detail:

FIG. 6: schematic representation of the detection of the phase shift without an analysis grating but with a structured detector element having scintillation strips which alternate with a grating structure, without frequency selection of the emitted light;

FIG. 8: schematic representation of the detection of the phase shift without an analysis grating but with a structured detector element having scintillation strips in groups of two, frequency selection of the emitted light according to two wavelengths, offset of the selection strips with a piezo element and a spring element;

DETAILED DESCRIPTION OF THE EXAMPLE EMBODIMENTS

Figure 1:
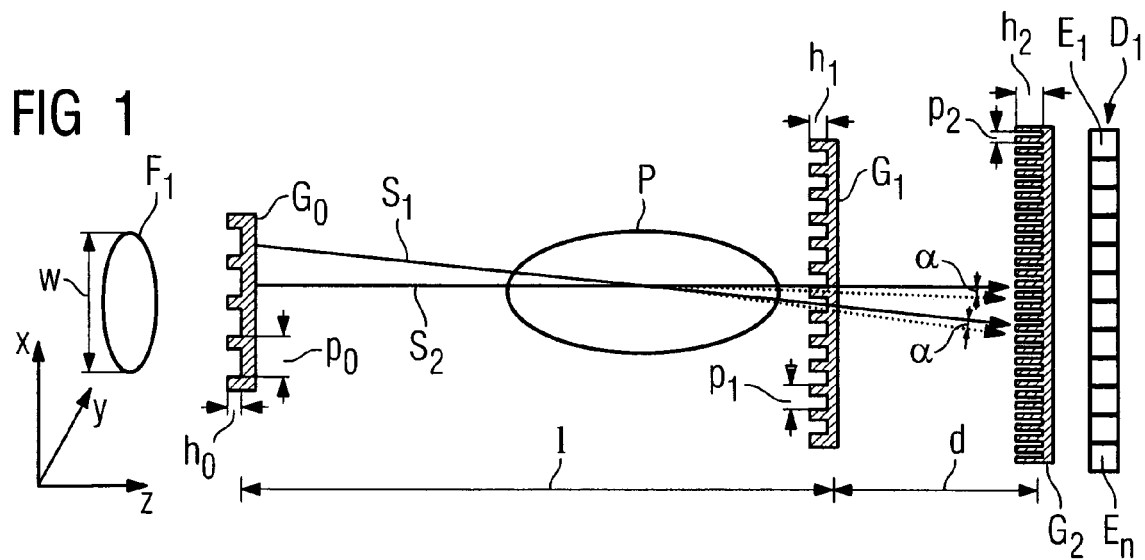
FIG. 1: longitudinal section through a focus/detector system with representation of the source grating, the phase grating and the analysis grating and their grating structure.

It will be understood that if an element or layer is referred to as being "on", "against", "connected to", or "coupled to" another element or layer, then it can be directly on, against, connected or coupled to the other element or layer, or intervening elements or layers may be present. In contrast, if an element is referred to as being "directly on", "directly connected to", or "directly coupled to" another element or layer, then there are no intervening elements or layers present. Like numbers refer to like elements throughout. As used herein, the term "and/or" includes any and all combinations of one or more of the associated listed items.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

The terminology used herein is for the purpose of describing particular embodiments only and is not intended to be limiting of the present invention. As used herein, the singular forms "a", "an", and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

Referencing the drawings, wherein like reference numerals designate identical or corresponding parts throughout the several views, example embodiments of the present patent application are hereafter described.

For better understanding of phase contrast measurement, a focus/detector system with a grating set $G_0$ to $G_2$ is shown in FIG. 1. Before the first grating $G_0$, there is a focus $F_1$ whose greatest extent is denoted by w. The first grating $G_0$ has a grating line period $p_0$ and a grating bar height $h_0$. The gratings $G_1$ and $G_2$ are correspondingly also provided with a height $h_1$ and $h_2$, respectively, and a period $p_1$ and $p_2$, respectively. In order for the phase measurement to function, it is necessary that the distance l between the gratings $G_0$ and $G_1$ and the distance d between the gratings $G_1$ and $G_2$ should be in a particular mutual ratio. Here, $$p_0 = p_2 \times \frac{l}{d}$$

The distance of the detector $D_1$ with its detector elements $E_1$ to $E_n$ from the last grating $G_2$ is not essential. The height $h_i$ of the bars of the phase grating should be selected so that the following formula is satisfied according to the wavelengths in question, i.e. the relevant energy of the X-radiation, and in relation to the respective grating material:

$$h_1 = \frac{\lambda}{2(n-1)}$$

Here, n denotes the refractive index of the grating material and λ denotes the wavelengths of the X-radiation, at which the phase shift is intended to be measured. This grating may advantageously be adjusted to an energy which corresponds to a characteristic line in the X-ray spectrum of the anode being used and at least a sufficient photon number should be available in this energy range. With the nowadays customary tungsten anodes, for example, the $K_\alpha$ line may be used. It is nevertheless also possible to use the $K_\beta$ line lying next to it. When other anode materials are selected, different energies and therefore different dimensioning of the phase grating will correspondingly be necessary.

The height $h_2$ of the analysis grating must be sufficient in order to generate effective absorption differences between the bars through which the X-radiation passes and the substantially free positions of the grating, in order to obtain a corresponding Moiré pattern on the rear side.

The line orientation of the gratings $G_0$ to $G_2$ is regularly configured so that the grating lines of all three gratings extend mutually parallel. It is furthermore advantageous, but not necessary, that the grating lines should be oriented parallel or perpendicularly to the system axis S, in which case the gratings $G_0$ to $G_2$ will usually be designed to be flat and aligned perpendicularly to the midline between the focus and detector midpoints. In principle, it is nevertheless also possible to adapt the surface of the gratings to the ray profile of the ray cone so that, at any position, the gratings are intersected perpendicularly by the ray connection between the focus and the respective detector element, which entails a corresponding curvature of the gratings.

Figure 2:
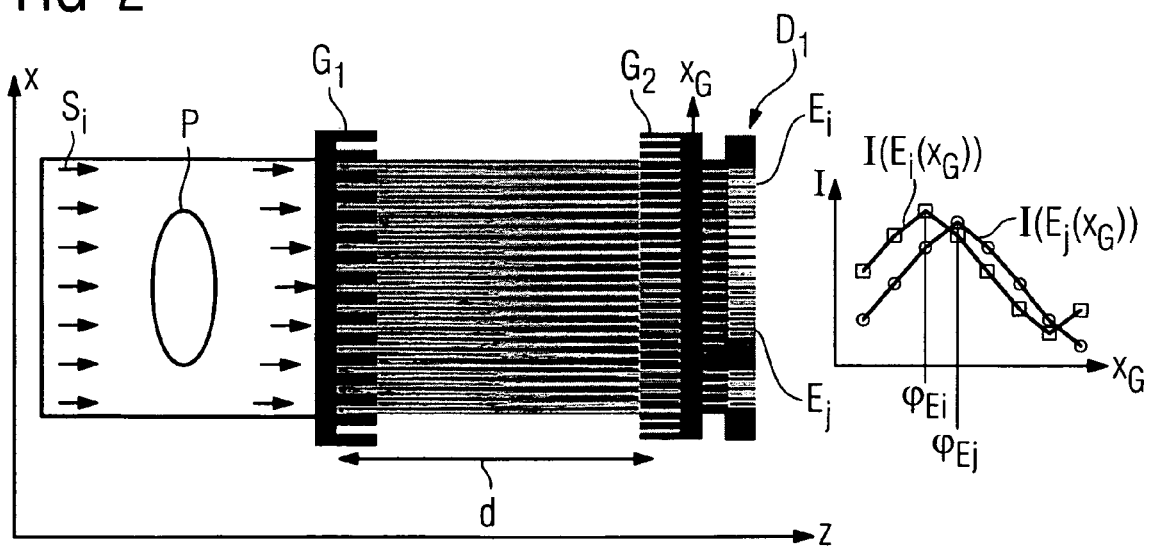
FIG. 2: longitudinal section through a focus/detector system of a CT with a phase grating, an analysis grating and a detector to represent the interference phenomenon.

FIG. 2 again shows the individually coherent radiation coming from the grating $G_0$, which passes through the patient P, phase shift phenomena taking place after it passes through the patient P. When passing through the grating $G_1$, an interference pattern is thereby generated, as represented by the gray shading, which with the aid of the grating $G_2$ leads to different radiation intensities per detector element on the downstream detector $D_1$ and its detector elements, a so-called Moiré pattern being formed there. If the detector element $E_i$, for example, is considered as a function of an offset $x_G$ of the analysis grating $G_2$ and the intensity $I(E_i(x_G))$ is plotted as a function of the offset $x_G$ against the intensity I, then a sinusoidal rise and fall of the intensity I at this detector element $E_i$ is obtained. If these measured radiation intensities I are plotted for each detector element $E_i$ or $E_j$ as a function of the offset $x_G$, then the function $I(E_i(x_G))$ or $I(E_j(x_G))$ can be approximated for the various detector elements, which in the end form the geometrical X-ray between the focus and the respective detector element. The phase shift φ relative to one another can be determined for each detector element from the functions. The following applies:

$$\varphi = 2\pi n \frac{v}{\lambda},$$

where v corresponds to the size of a voxel or pixel in the object examined, n is its refractive index and λ represents the wavelength of the X-radiation.

For each ray in space, the phase shift per ray can therefore be determined by at least three measurements with a respectively offset analysis grating, from which either the pixel values of a projective recording can be calculated directly in the case of projective X-ray recordings, or projections whose pixel values correspond to the phase shift are compiled in the case of a CT examination, so that with the aid of reconstruction methods known per se it is possible to calculate therefrom which volume element in the subject is to be ascribed to which component of the measured phase shift. Either section images or volume data are thus calculated therefrom, which reflect the local effect of the examined object in respect of the phase shift of X-radiation. Since even minor differences exert a strong effect on the phase shift in this context, very detailed and high-contrast volume data can be obtained from materials which are relatively similar per se, in particular soft tissue.

The previously described variant of detecting phase shifts of the X-rays which pass through a subject, with the aid of a multiply offset analysis grating and measuring the radiation intensity on a detector element behind the analysis grating, has the disadvantage that at least three measurements of each X-ray have to be carried out with a respectively displaced analysis grating. This makes the scanning of the subject relatively slow, the dosage also being increased. There is also the problem that a part of the radiation is lost from the detection owing to the analysis grating being used, since it is absorbed in the grating.

At least one embodiment of the invention therefore proposes to obviate such an analysis grating and instead to structure the detector elements, which are arranged following the phase grating, so that at least no dose loss occurs in the measurement, and advantageously to select a division such that the phase shift in the relevant ray can be determined by a single measurement.

Figure 3:
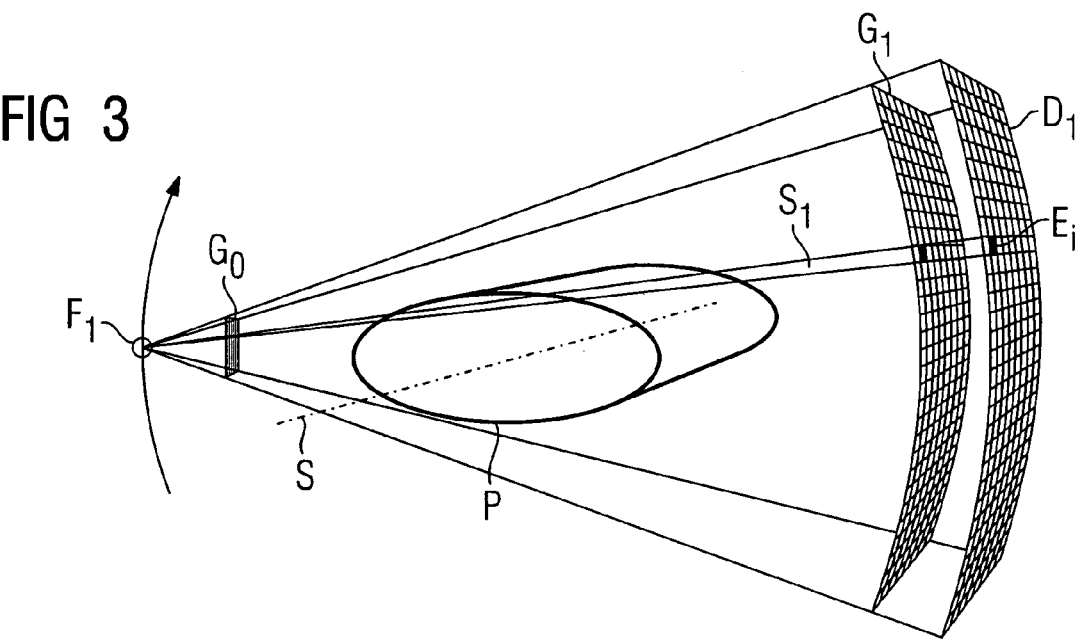
FIG. 3: schematic 3D view of a focus/detector system according to the invention without an analysis grating.

Such an arrangement is schematically shown in a 3D representation of a focus/detector system of a computer tomograph in FIG. 3. This shows a focus $F_1$ in whose beam path a source grating $G_0$ is arranged and on the detector side there is a phase grating which generates the interference phenomena described above, which are measured by the subsequent detector so that each individual detector element can measure the phase shift, or more precisely the average phase shift, of the radiation over this detector element. In the representation shown, a detector $D_1$ which is designed as a multiline detector is represented on the detector side, each line containing a multiplicity of detector elements and each detector element being preceded by a grating structure of the phase grating $G_1$.

Figure 4:
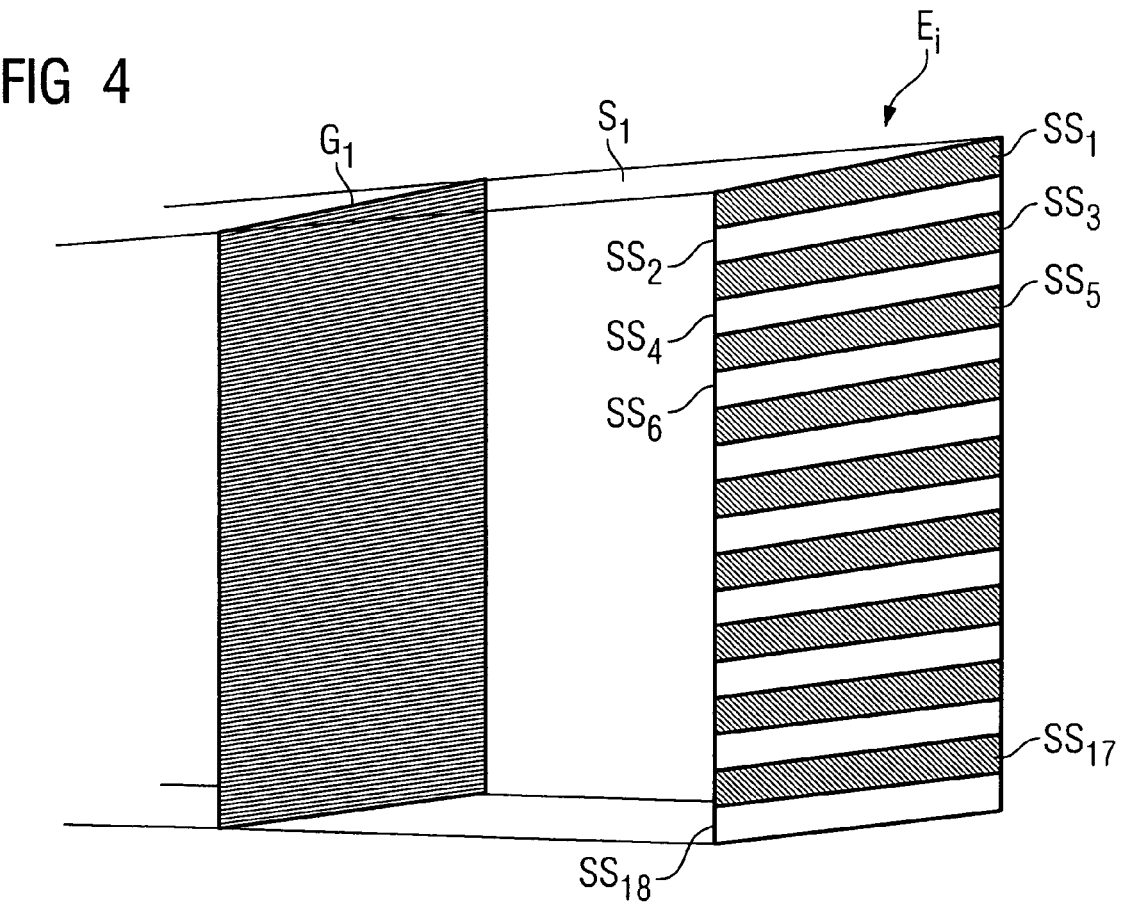
FIG. 4: three-dimensional representation of an individual detector element with an upstream phase grating.

This combination of a grating and detector element is shown on an enlarged scale in FIG. 4. Here, the detector element is represented as being structured, consisting of a multiplicity of scintillation strips $SS_1$ to $SS_{18}$ which are oriented in terms of their alignment parallel to the grating lines of the phase grating $G_1$. It should be pointed out that the division as shown here is merely a schematic representation, which is intended to show the basic principle of the division, the dimensions in practice being fundamentally different therefrom.

In practice, the size of such a detection element is in the range of from 100 to 1000 μm. The period $p_2$, of the order of which the extent of the scintillation strips must be, is generally about 2 μm so that the individual scintillation strips, if they are divided into two divisions, are approximately one μm.

Figure 5:
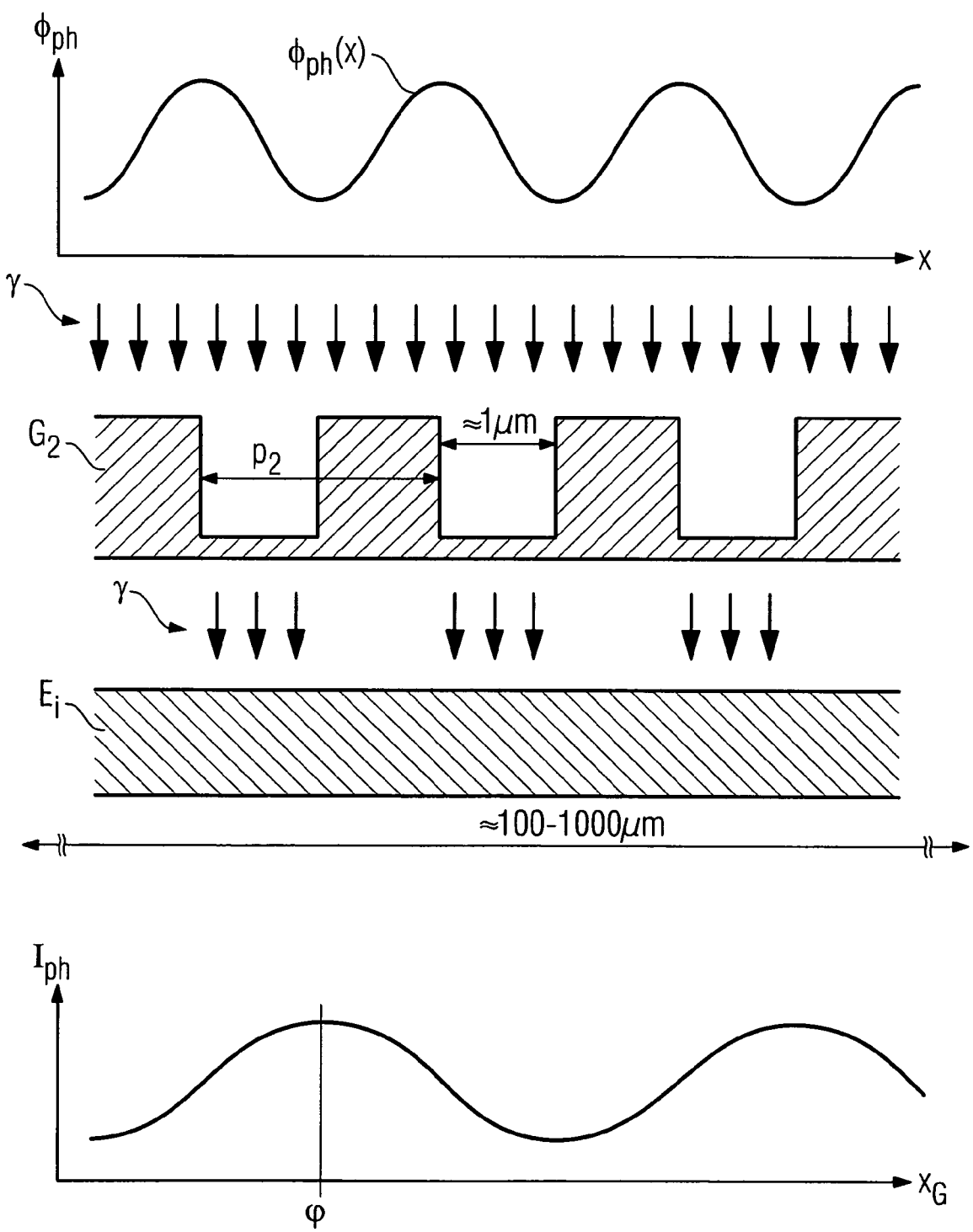
FIG. 5: schematic representation of the detection of the phase shift with an analysis grating.

FIG. 5 further illustrates the basic principle of measuring the phase shift with the aid of an analysis grating $G_2$. This representation schematically shows the flux of the X-ray photons $\Phi_{ph}$ over the x axis behind the phase grating at a spacing of one Talbot distance, the profile of the photon flux $\Phi_{ph}(x)$ being plotted against the x axis. The x axis in this case extends perpendicularly to the grating lines. The analysis grating $G_2$ is subsequently shown, which comprises a period $p_2$ and absorbs the photons in its bars so that only at the free positions can the photons pass through downward and finally strike the detector element $E_i$ lying behind, where their intensity is measured. If the grating $G_2$ is now displaced slightly in the direction of the x axis, then a strong intensity variation of the measured radiation intensity $I_{ph}$ occurs on the detector element lying behind, which may be plotted against the length of the displacement of the grating. The phase φ can be determined for the respective detector element from the curve of the radiation intensity as a function of the offset $x_G$ of the analysis grating $G_2$.

According to at least one embodiment of the invention, the analysis grating can now be replaced by imparting a grating-like structure to the detector element, so that for the detection of radiation there are periodically arranged strip-shaped regions which groupwise provide information about the radiation incident there. In the simplest variant, this involves a single group of strips $SS_i$ which alternate with grating strips without detection $GS_i$. The period of the replaced analysis grating, tuned to the respective energy of the grating arrangement, is selected as the period $p_2$ with which these strips are arranged. Here, the width of the scintillation strips may advantageously be selected so that it is equal to half the period of the corresponding analysis grating.

Such a situation of a detector element $E_i$ is represented in FIG. 6. The photon flux $\Phi_{ph}$ due to the interference phenomenon, which is caused by the phase grating, is here again firstly represented at the top against the x axis. This position-dependent photon flux $\Phi_{ph}(X)$, also represented using the arrows denoted by γ, strikes the detector element with differing intensity and is periodically converted into light with the wavelength $\lambda_1$ by the multiplicity of scintillation strips $SS_1$ to $SS_6$. This light shines into a space 17, which as far as possible is mirrored on all sides, where it is measured as a whole by a photodiode 12.

Since this embodiment with respect to the division of detecting and non-detecting regions essentially constitutes no difference from the analysis grating described above, here again it is necessary to measure changes in the radiation intensity relative to the spatial offset of the scintillation strips. In this example, this is done by offsetting the detection element $E_i$ as a whole relative to the detector housing 14 with the aid of two piezo elements 13.1 and 13.2, and measuring the radiation intensity on the scintillation strips at each offset. These intensity measurements $I_{ph}(x_G=0)$, $I_{ph}(x_G=\frac{1}{4}p_2)$, $I_{ph}(x_G=\frac{2}{4}p_2)$ and $I_{ph}(x_G=\frac{3}{4}p_2)$, with a relative offset $x_G$ of $p_2/4$, are plotted at the bottom in FIG. 6. From this, it is possible to approximate a sine curve and calculate the phase shift.

It should also be noted that measurement of three sample points is sufficient in principle, although more sample points can be advantageous for reducing the noise and compensating for other measurement errors.

It should furthermore be pointed out that a detection element as represented in FIG. 6 may, for example, be produced by filling the free positions of a grating generated by etching technology, which produces the grating strips $GS_i$, with a polymer that contains nanoparticles of scintillation material.

Figure 7:
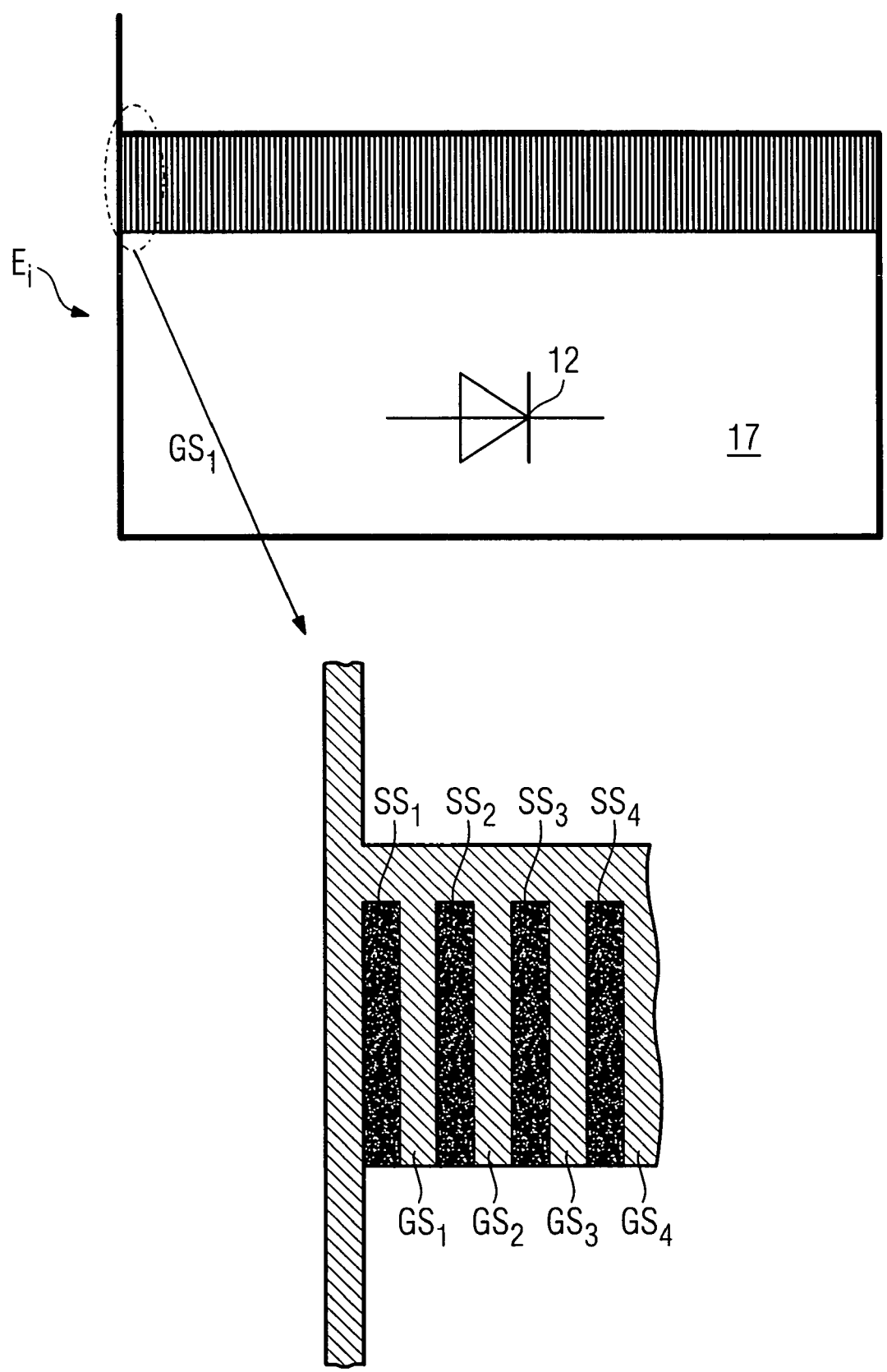
FIG. 7: sectional representation of a detector element of FIG. 6 with an enlarged detail excerpt.

FIG. 7 shows an embodiment of such a detector element $E_i$ which is somewhat more realistic in respect of the dimensioning. The structure of the grating having the gaps filled with scintillation material is also represented in a detail enlargement.

An improved embodiment of a detector element $E_i$ according to an embodiment of the invention is schematically presented in FIG. 8. This differs from FIG. 6 in that the scintillation strips are not supported between one another by a grating structure insensitive to radiation, rather it consists exclusively of scintillation strips constructed in layer fashion. The small period $p_{ss}$ of the scintillation strips corresponds here to half the period $p_2$ of a corresponding analysis grating, also referred to as the large period. For example, this involves a polymer material which is alternately filled with different nanoparticles that emit different light with the wavelengths $\lambda_1$ and $\lambda_2$ in a space 17 when exposed, the layered structure being obtained for example by successive laser irradiation of different liquid polymer-nanoparticle mixtures—similarly as prototype construction.

The light emitted during the X-ray exposure is radiated into a mirrored space which through two frequency-selective filters 16.1, 16.2 of two photodiodes 12.1 and 12.2, which respectively present a measurement path A or B. In this way, light of the wavelength $\lambda_1$ is received only via the measurement path A and light of the wavelength $\lambda_2$ is received only via the measurement path B. Correspondingly, the radiation intensities at the even-numbered or odd-numbered scintillation strips may be determined simultaneously by a measurement.

In this way, by considering the dose measured respectively via the measurement path A or the measurement path B, it is possible to measure the intensity change which would result if an analysis grating—corresponding to FIG. 5—would be displaced by one half period. If two further measurements A', B' are now carried out with an offset of $p_2/4$, then four measurement values A, B, A' and B' are available at four sample points. The average phase φ of the X-ray of this detector element can be calculated directly therefrom. This is represented at the bottom of FIG. 8. In this special embodiment, the offset of the scintillation strips is generated by electrically controlling a piezo element 13 on one side of the layered scintillation strips and compensating by a spring element 15 on the other side.

A substantial advantage of this embodiment variant is that no radiation dose which has passed through a patient is lost, since the entire surface of the detection elements is used for determining the phase shift.

Figure 9:
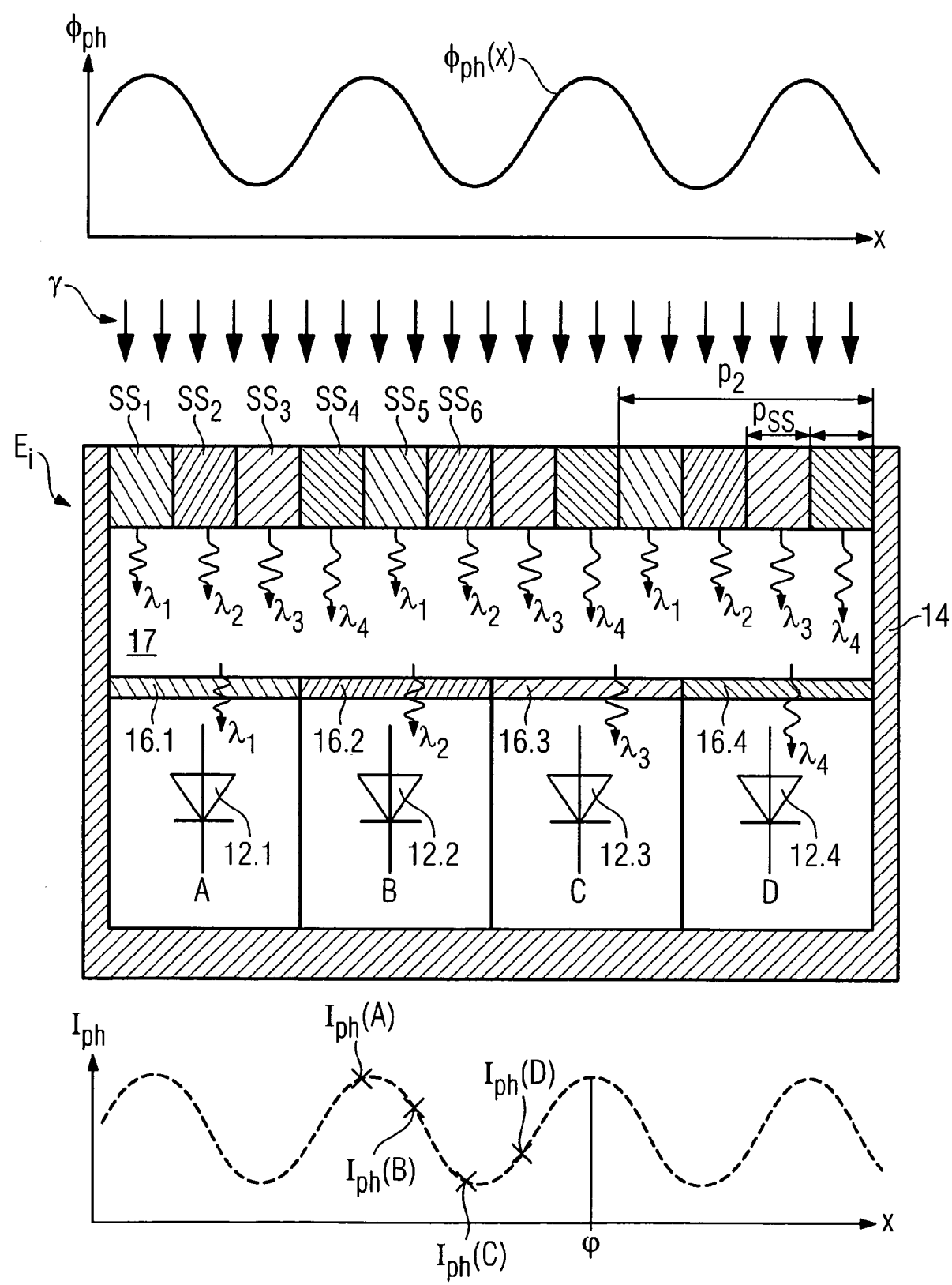
FIG. 9: schematic representation of the detection of the phase shift with a detector element having scintillation strips divided into groups of four, frequency selection of the emitted light according to four wavelengths, no offset of the selection strips being necessary.

While it is still necessary to carry out at least two measurements with respectively offset scintillation strips in the alternative embodiment of FIG. 8, this is not necessary in a further improved embodiment of the inventive detection system in FIG. 9. Here, the phase of the X-radiation detected by a detection element can be determined via a single measurement. Similarly as FIG. 8, FIG. 9 shows a detection arrangement with the radiation arriving from above on a detection element $E_i$, the radiation generating small-space interference phenomena owing to the upstream energy-specific grating arrangement, which leads to the periodically varying photon flux as described above. Realistically, this variation is not strictly periodic but, because of the phase shift occurring with differing strength, is subject to spatial fluctuations from which the phase shift of a ray can reciprocally be determined.

In the present example, the subdivision of the detection element into scintillation strips is configured so that the individual scintillation strips merely have a width or small period $p_{ss}$ of ¼ of the period $p_2$ of a corresponding analysis grating. Here, four differently doped scintillation materials are used, which respectively generate light at different frequencies and wavelengths because of the different doping. The four different scintillation strips are repeatedly sequenced with the same period and in the same order. Each group of scintillation strips with the same doping emits light of the same wavelength, and the four groups emit light of four different wavelengths $\lambda_1, \lambda_2, \lambda_3,$ and $\lambda_4$. Selected according to wavelength with the aid of the filters 16.1 to 16.4, this light is measured at four different photodiodes 12.1 to 12.4, corresponding to the measurement paths A to D, and therefore represents a measure of the dose arriving on the various scintillation strips.

In this way, the scintillation strips are thus interconnected so that every fourth strip uses the same measurement path. If a measurement is now carried out with such a detector arrangement at a particular position, i.e. for a particular X-ray, then the phase-corresponding intensity can respectively be read from the intensities measured via the measurement paths A, B, C and D and the phase of the X-radiation which strikes this detector element can be determined directly from these four measurements. The evaluation of these four measurement values A, B, C, D is represented at the bottom in this figure. It should furthermore be noted here that this measurement does not correspond for instance to a phase determination of the X-radiation in the region of an individual scintillation strip, rather it represents averaging over the entire surface of the detection element. In this alternative embodiment as well, it is particularly advantageous that the entire dose used for the measurement which irradiates the subject, in particular a patient, is employed for the evaluation and scarcely no dose losses occur.

The essence of the two alternative embodiments presented last is thus that a detector element is divided into a multiplicity of scintillation strips, which are read groupwise in respect of the measured X-ray intensity, the division needing to be carried out so that on the one hand it matches the period $p_2$ of a corresponding analysis grating, but at the same time it comprises at least two and preferably at least three scintillation strips per period so that each of the groups of scintillation strips is represented once per period. This type of division thus makes it possible to fit two, three, four, five or more scintillation strips within one period and sequence this division repeatedly in a direction perpendicular to the alignment of the scintillation strips, so that the number of measurement groups corresponds to the number of scintillation strips per period $p_2$.

Figure 10:
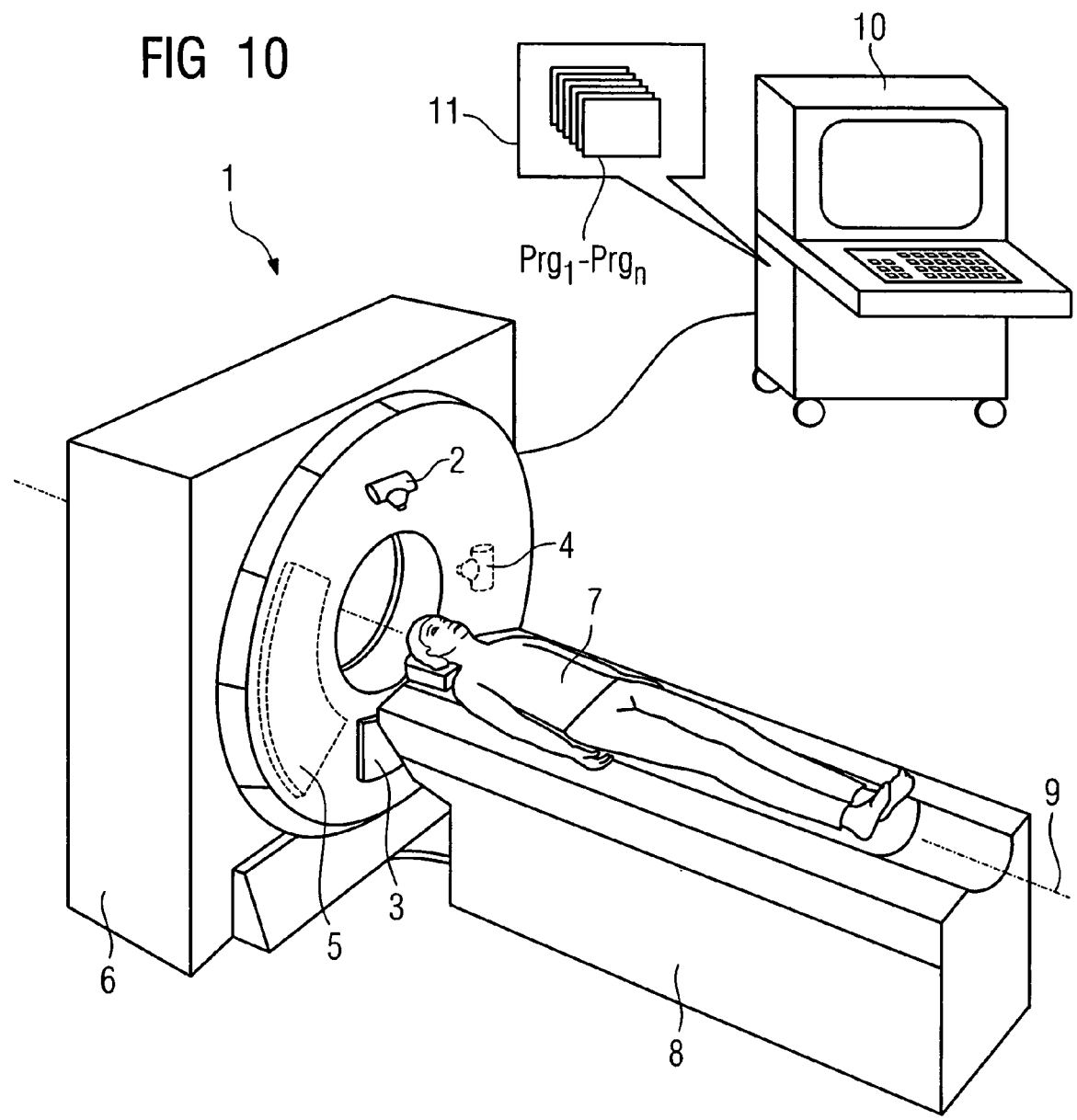
FIG. 10: X-ray CT system in 3D view with a focus/detector system according to an embodiment of the invention.

FIG. 10 represents a complete computer CT system for carrying out the method according to an embodiment of the invention. It shows the CT system 1 which comprises a first focus/detector system with an X-ray tube 2 and a detector 3 lying opposite, which is arranged on a gantry (not represented in detail) in a gantry housing 6. An X-ray optical grating system according to the invention is arranged in the beam path of the first focus/detector system 2, 3 so that the patient 7, who lies on a patient support 8 displaceable along the system axis 9, can be displaced into the beam path of the first focus/detector system and scanned there. The CT system is controlled by a computation and control unit 10 in which programs $Prg_1$ to $Prg_n$ are stored in a memory 11, which carry out the method according to an embodiment of the invention as described above and reconstruct corresponding tomographic images from the measured ray-dependent phase shifts.

Optionally, instead of the single focus/detector system, a second focus/detector system may be arranged in the gantry housing. This is indicated in FIG. 10 by the X-ray tube 4 shown in dashes and the detector 5 represented in dashes.

Moreover, it should also be pointed out that the focus/detector systems as presented are not only capable of measuring phase shifts of the X-radiation, rather they are furthermore suitable for conventional measurement of the radiation absorption and reconstruction of corresponding absorption recordings. Optionally, combined absorption and phase contrast recordings may even be generated.

It should furthermore be pointed out that in practical embodiment, the gaps between the grating lines in the source gratings used may be filled with a highly absorbent material to improve the contrast. For example, gold may be used for this. In principle, the source gratings should be configured so that they achieve a contrast factor of at least $e^{-1}$.

It is to be understood that the features of the invention as mentioned above may be used not only in the combination respectively indicated, but also in other combinations or in isolation, without departing from the scope of the present invention.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A focus/detector system of an X-ray apparatus for generating at least one of projective and tomographic phase contrast recordings, of the system comprising:
   a beam source, including a focus and a focus-side source grating arranged in the beam path, to generate a field of ray-wise coherent X-rays;
   a grating/detector arrangement including a phase grating and grating lines arranged parallel to the source grating to generate an interference pattern, and a detector including a multiplicity of detector elements arranged flat to measure the position-dependent radiation intensity behind the phase grating, the detector elements being formed by a multiplicity of elongate scintillation strips, being aligned parallel to the grating lines of the phase grating, and including a small period, an integer multiple of the detector elements corresponding to an average large period of the interference pattern formed by the phase grating.

2. The focus/detector system as claimed in the preceding patent claim 1, wherein the grating/detector arrangement is designed and arranged so that it satisfies the following geometrical conditions:

$$p_2 = k \times p_s$$
$$p_0 = p_2 \times \frac{l}{d},$$
$$p_1 = 2 \times \frac{p_0 \times p_2}{p_0 + p_2}$$
$$d = \frac{l \times d^=}{l - d^=} \text{ with } d^= = \frac{1}{2} \times \left(\frac{p_1^2}{4\lambda}\right),$$
$$h_1 = \frac{\lambda}{2(n-1)},$$

where:
$p_0$=grating period of the source grating $G_0$,
$p_1$=grating period of the phase grating $G_1$,
$p_2$=large period of the scintillation strips $SS_i$, average spacing of the interference lines after the phase grating,
$p_s$=small period of the scintillation strips $SS_i$, distance from midline to midline of neighboring scintillation strips,
d=distance from the phase grating $G_1$ to the detector in fan beam geometry,
$d^=$=distance from the phase grating $G_1$ to the detector with parallel geometry,
k=1, 2, 3, 4, 5, . . . ,
l=distance from the source grating $G_0$ to the phase grating $G_1$,
λ=selected wavelength of the radiation,
$h_1$=bar height of the phase grating $G_1$ in the beam direction,
n=refractive index of the grating material of the phase grating.

3. The focus/detector system as claimed in claim 2, wherein precisely one scintillation strip, which alternates with a detector grating structure made of non-scintillating material, is arranged inside each large period.

4. The focus/detector system as claimed in claim 2, wherein precisely two scintillation strip different scintillation material, which generate light of different frequency, are arranged inside each large period and their sequence remains the same over the detector element.

5. The focus/detector system as claimed claim 1, wherein precisely one scintillation strip, which alternates with a detector grating structure made of non-scintillating material, is arranged inside each large period.

6. The focus/detector system as claimed in claim 5, wherein the detector grating structure is made of metal.

7. The focus/detector system as claimed claim 1, wherein precisely two scintillation strips of different scintillation materials, which generate light of different frequency, are arranged inside each large period and their sequence remains the same over the detector element.

8. The focus/detector system as claimed in claim 7, further comprising:
means, in the detector element, for detecting the light emissions of the scintillation strips of a detector element with different frequency separately according to frequency but summed over the entire detector element.

9. The focus/detector system as claimed in claim 8, wherein the scintillation strips emit their light with different frequencies at least partially into a mirrored space which adjoins frequency-selective light sinks, and each light sink comprises means for detecting the selected light.

10. The focus/detector system as claimed in claim 9, wherein the light sinks respectively include a filter with a downstream photodiode, the filters respectively being selective for precisely one of the emitted frequencies of the scintillation strips.

11. The focus/detector system as claimed in the preceding patent claim 9, wherein the light sinks are arranged in cascade fashion and respectively comprise a filter on the scintillator side with a photodiode, which limits the frequencies on one side so that a reduced number of frequencies is measured in the subsequent filter/photodiode set.

12. The focus/detector system as claimed in claim 1, further comprising:
means for offsetting the scintillation strips perpendicularly to the longitudinal direction of the scintillation strips in the detector, to generate a defined offset of the order of the small period of the scintillation strips.

13. The focus/detector system as claimed in claim 12, wherein the means for offsetting are piezo elements.

14. The focus/detector system as claimed in claim 1, further comprising:
means for offsetting the detector elements perpendicularly to the longitudinal direction of the scintillation strips in the detector, to generate a defined offset of the order of the small period of the scintillation strips.

15. The focus/detector system as claimed in claim 14, wherein the means for offsetting are piezo elements.

16. The focus/detector system as claimed in claim 1, further comprising:
means for offsetting the detector perpendicularly to the longitudinal direction of the scintillation strips in the detector, to generate a defined offset of the order of the small period of the scintillation strips.

17. The focus/detector system as claimed in claim 16, wherein the means for offsetting are piezo elements.

18. The focus/detector system as claimed in claim 1, wherein at least three scintillation strips, made of different scintillation materials, which generate light of different frequency, are arranged inside each large period and their sequence preferably remains the same over the detector element.

19. The focus/detector system as claimed in claim 18, further comprising:
means for offsetting the scintillation strips perpendicularly to the longitudinal direction of the scintillation strips in the detector, to generate a defined offset of the order of the small period of the scintillation strips.

20. The focus/detector system as claimed in claim 19, wherein the means for offsetting are piezo elements.

21. The focus/detector system as claimed in claim 18, further comprising:
means for offsetting the detector elements perpendicularly to the longitudinal direction of the scintillation strips in the detector, to generate a defined offset of the order of the small period of the scintillation strips.

22. The focus/detector system as claimed in claim 21, wherein the means for offsetting are piezo elements.

23. The focus/detector system as claimed in claim 18, further comprising:
means for offsetting the detector perpendicularly to the longitudinal direction of the scintillation strips in the detector, to generate a defined offset of the order of the small period of the scintillation strips.

24. The focus/detector system as claimed in claim 23, wherein the means for offsetting are piezo elements.

25. An X-ray system for generating projective phase contrast recordings comprising at least one focus/detector system as claimed in claim 1.

26. The X-ray system as claimed in claim 25, further comprising a computation unit to control the detector and to calculate the phase shift from a plurality of intensity measurements of the same ray.

27. An X-ray C-arc system for generating projective and tomographic phase contrast recordings comprising at least one focus/detector system as claimed in claim 1, arranged on a C-arc rotatable about a subject.

28. The X-ray C-arc system as claimed in claim 27, further comprising a computation unit to control the detector and to calculate the phase shift from a plurality of intensity measurements of the same ray.

29. An X-ray CT system for generating tomographic phase contrast recordings comprising at least one focus/detector system as claimed in claim 1, arranged on a gantry rotatable about a subject.

30. The X-ray CT system as claimed in claim 29, further comprising a computation unit to control the detector and to calculate the phase shift from a plurality of intensity measurements of the same ray.

31. A method for generating projective X-ray recordings of a subject using a focus/detector system, the method comprising:
irradiating the subject by a beam of rays, each ray in space being defined with respect to direction and extent by a focus-detector element connecting line and the extent of the detector element;
measuring an average phase shift of each ray in that, for each ray, intensity of radiation is measured with the aid of fine structured scintillation strips at scintillation strips arranged groupwise and offset with respect to one another or positioned offset from one another;
compiling phase contrast recordings, the pixel values of which represent the average phase shift per ray, from the measured average phase shifts; and
reconstructing at least one image based on the compiled phase contrast recordings.

32. The method as claimed in claim 31, wherein the various scintillation strips of a detector element emit light groupwise with different light frequencies during exposure and this light is measured selectively with respect to the frequency but summed over the entire detector element.

33. The method as claimed in claim 32, wherein a spatial offset of the scintillation strips perpendicularly to the grating line direction is induced between two measurements of the same ray.

34. The method as claimed in claim 33, wherein the spatial offset of the scintillation strips is induced by an amount less than the period of the scintillation strips.

35. The method as claimed in the preceding patent claim 32, wherein there are at least three different types of scintillation strips in a detector element, arranged uniformly alternating and one measurement for all emitted light frequencies is carried out per detector element and position, and the average phase shift of the measured X-ray is determined directly therefrom.

36. An X-ray system comprising a computation and control unit storing executable instructions, which when executed by the computation and control unit, causes the computation and control unit to carry out the method as claimed in claim 31.

37. A computer-readable medium storing executable instructions, which when executed by an X-ray system, cause the X-ray system to carry out the method as claimed in claim 13.

* * * * *